United States Patent [19]
Dewey et al.

[11] Patent Number: 4,686,992
[45] Date of Patent: Aug. 18, 1987

[54] OPHTHALMIC BEAM DIRECTOR

[75] Inventors: David A. Dewey, Huntington Beach; Paul C. Pynckel, Santa Ana, both of Calif.

[73] Assignee: CooperVision, Inc., Palo Alto, Calif.

[21] Appl. No.: 729,985

[22] Filed: May 3, 1985

[51] Int. Cl.$^4$ .................... A61B 17/36; G02B 7/18
[52] U.S. Cl. .................... 128/303.1; 128/395; 219/121 LQ; 350/486; 350/636
[58] Field of Search .............. 128/303.1, 395–398; 219/121 LQ; 350/486, 636

[56] References Cited

U.S. PATENT DOCUMENTS

| | | | |
|---|---|---|---|
| 2,220,382 | 11/1940 | Zimmerman | 90/38 |
| 2,441,719 | 5/1948 | Potter | 74/501 |
| 2,928,318 | 3/1960 | Friday | 88/93 |
| 3,096,767 | 7/1963 | Gresser | 128/395 |
| 3,315,680 | 4/1967 | Silbertrust et al. | 128/395 |
| 3,403,579 | 10/1968 | Casalou | 74/501 |
| 3,487,835 | 1/1970 | Koester | 128/303.1 |
| 3,703,176 | 11/1972 | Vassiliadis et al. | 128/395 |
| 3,796,220 | 3/1974 | Bredemeier | 128/303.1 |
| 4,141,362 | 2/1979 | Wurster | 128/303.1 |
| 4,396,285 | 8/1983 | Presta et al. | 356/138 |
| 4,397,310 | 8/1983 | Pomerantzeff | 128/303.1 |
| 4,406,525 | 9/1983 | Itoh et al. | 350/486 |
| 4,526,447 | 7/1985 | Taylor | 128/303.1 X |

FOREIGN PATENT DOCUMENTS 0069987  1/1983  European Pat. Off. .......... 128/303.1

Primary Examiner—Lee S. Cohen
Attorney, Agent, or Firm—Vorys, Sater, Seymour & Pease

[57] ABSTRACT

A micromanipulator for an instrument for focusing a beam of light on a target, such as a laser in an ophthalmic instrument, includes a control member coupled through a spherical bearing located at a pivot location to a coiled spring connected to a control rod for manipulating the focus of a gimballed beamsplitter in the x and y directions. The components are structured and arranged to lie on an axis in the neutral position so that the movement of the light beam, during focusing, corresponds directly to the direction of movement of the control member by an operator. The coiled spring acts as an automatic centering device to return the focused light beam to a predetermined position in the absence of manipulation.

15 Claims, 8 Drawing Figures of the invention is read in conjunction with the drawings.

OPHTHALMIC BEAM DIRECTOR

BACKGROUND OF THE INVENTION

1. Field of the Invention

This invention relates to a control of a beam used in ophthalmic procedures. More particularly, this invention relates to a micromanipulation of light beams that are used for ophthalmic inspection in diagnostic procedures and for photocoagulation. Still more particularly, this invention relates to a spring-biased apparatus for controlling the position of a focused laser beam to follow directly the movement of an operator's hand during manipulation and to return the focused beam to a predetermined location such as a center in the absence of manipulation of a control member.

2. Discussion of Related Art

In medical and diagnostic procedures, as well as in other arts, the use of focused beams of light is well-known and various types of mechanisms for focusing the light beams have been developed. In the medical arts, the use of lasers and xenon-arc lamps to treat retinal detachment and to treat tumors is now well known. In either case, the surgical light beam is momentarily optically coupled into the path an ophthalmic slit lamp which is used to aim the surgical beam. The slit lamp also provides illumination for inspecting the eye through a binocular microscope. U.S. Pat. No. 3,703,176, issued Nov. 21, 1972, to Vassiliadis et al, is an example of this kind of device, and illustrates the general structure of an optometric slit lamp in FIGS. 1 and 3. As shown, a slit lamp is an instrument for examining the eye under magnification, using a microscope (generally binocular, as illustrated) and an integral source of illumination, which directs a beam of light into the eye. The particular embodiment illustrated in Vassiliadis is a special slit lamp equipped with a laser photocoagulator, but such instruments have the same general structure. It is this general structure to which this invention is directed.

Both the slit lamp and surgical beams are directed by a spring-mounted lens in this type of device. The operator moves the lens by means of a control member, such as a joystick, having a ball joined at its fulcrum and a ball joint connection to the lens mounting. This type of beam direction control has proved unsatisfactory in that, first of all, the manually-operated control member and the beam move in opposite directions and, secondly, there is a tendency for the "home" or centered position of the beam to drift due to cumulative fatigue or to unequal loading of the mounting springs for mounting the lens. The reversal of movement between the control member and the light beam produces a sensory dissonance which has made eye/hand coordination difficult for persons using such well-known surgical laser apparatus.

In the current model of such a device available from the assignee of this invention, the micromanipulator moves the beam opposite to the direction of the hand movement of the operator. Accordingly, it is an objective of this invention to provide a micromanipulator which, contrary to that available device, moves the focused beam in the same direction as the hand movement of the operator on the control member. Thus, when the control member is moved left or right along an x-axis, the focused beam also correspondingly moves left or right. Similarly, when the control member is moved up or down along the y-axis, the focused beam correspondingly moves up or down. The mounting of such a control member, or joystick, permits the operator to select any location on a grid having x and y coordinates, so that it should be understood that movement of the control member is not confined to either axis.

In such a device, it would also be advantageous for the focused beam to return to a predetermined location, such as a center of coordinates, when manual control effort has ceased. Accordingly, it is another feature of this improvement to bias the focusing device to center the beam in the absence of a control effort by the operator.

A laser beam scanning mechanism is also shown in European Patent Publication No. 0,069,987, published Jan. 19, 1983, in which an operator shifts the position of a point irradiated by a laser beam by moving a joystick control member. As described, the position of the focused beam is determined by the angle of inclination of a mirror rotatably supported about both a horizontal and vertical axis. The use of such a gimbal mechanism is described in that publication by reference to Japanese Patent Application Laid-Open No. 106144/19180. Such device apparently requires two orthogonal rotary shafts and several levers in combination. To the contrary, satisfactory horizontal and vertical positioning of a beamsplitter in the applicants' invention is achieved with a single, biased control rod.

These and other objectives and features of the invention will become apparent from the written description which follows.

SUMMARY OF THE INVENTION

The micromanipulator apparatus according to the invention is applied to an ophthalmic device for micromanipulating a position of a light beam directed against a target. The apparatus to which the invention is applied includes a source of light such as a laser, and a beamsplitter for receiving light from the source and redirecting the light to a target. The beamsplitter is pivotable about an x-axis for vertically redirecting the light and rotatable about a y-axis for horizontally redirecting the light and, in a preferred embodiment, the beamsplitter is gimbal-mounted for controlled movement about the x and y-axes respectively by the apparatus according to the invention.

The apparatus of the invention comprises means for manually micromanipulating the beamsplitter and includes a control member capable of movement in a direction having both an x component and a y component; a spherical bearing coupled to said control member at a pivot location; a coiled spring coupled to the control member through the spherical bearing to bias the micromanipulator toward centering the focused beam; and a control rod coupled to the spring and to the gimbaled mirror. In a preferred embodiment, the components are arranged to lie on a single axis when the micromanipulator is in its neutral position. In addition, the components are arranged so that the focused beam respectively follows the hand movement of the operator on the control member with respect to leftward, rightward, upward, and downward movements.

A method of using a micromanipulator according to this invention is also described.

BRIEF DESCRIPTION OF THE DRAWINGS

The nature and advantages of the present invention will be better understood when the detailed description of the present invention is considered in conjunction with the drawings provided, wherein.

In these figures, similar parts are assigned the same numbers.

DETAILED DESCRIPTION OF THE PREFERRED EMBODIMENT

Figure 1:
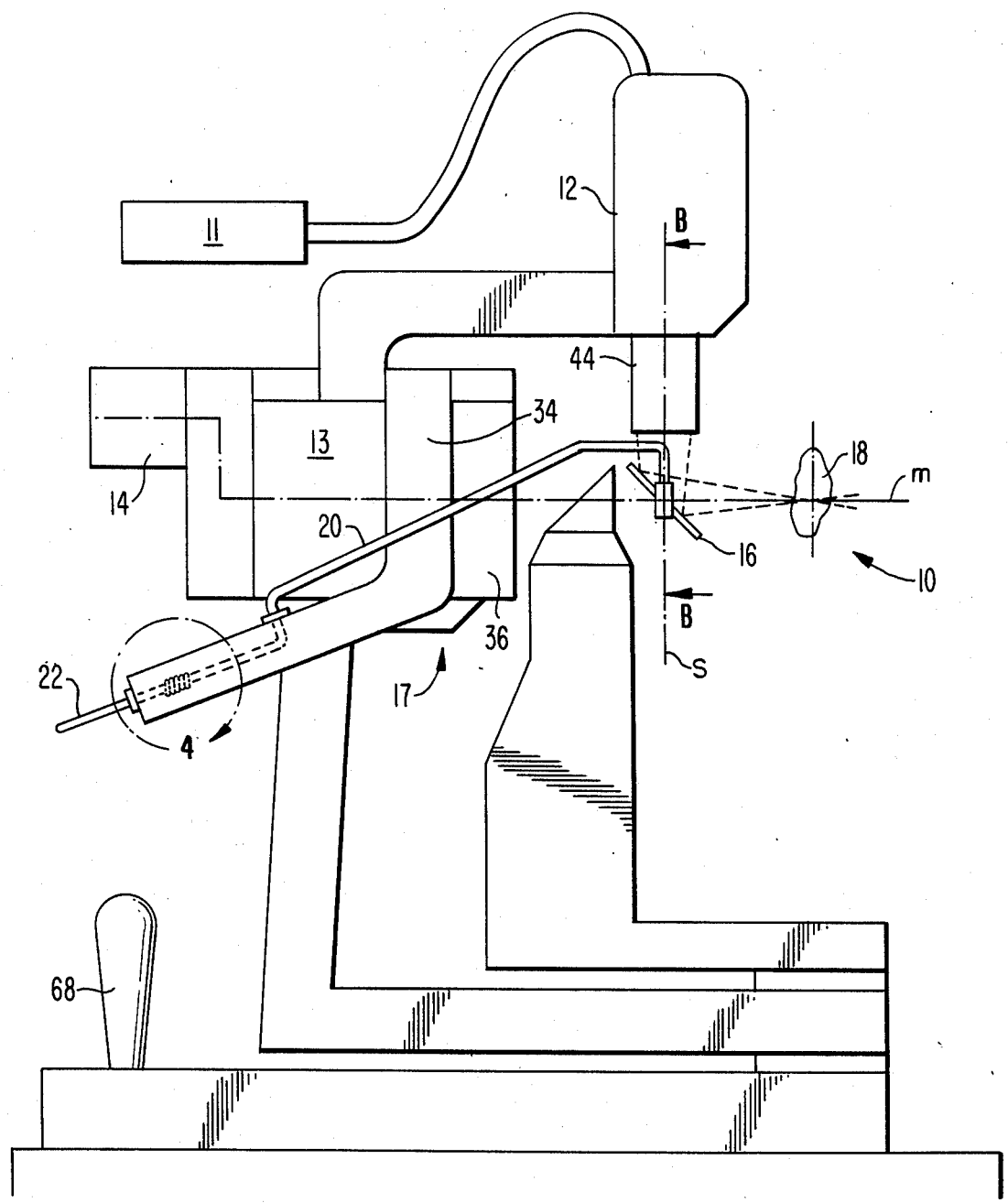
FIG. 1 is a schematic diagram of a side view of an apparatus, including the micromanipulator of the invention, for focusing a light beam, and showing the optical axes of the apparatus.

In FIG. 1, a preferred embodiment to which the micromanipulator apparatus of the present invention is applied is shown generally by a reference numeral 10. The device comprises a laser 11, such as an argon laser, optically connected to a laser beam delivery assembly 12 having a slit lamp 13. The laser beam delivery assembly 12 is mounted for cooperation with a binocular microscope 14, as is known in the art for such combinations.

A beamsplitter 16, such as a pivotally and rotatably mounted mirror, is mounted at the intersection of the optical axes s, m of the microscope 14 and the laser beam delivery assembly 12 so that light from the laser beam delivery assembly is reflected by the beamsplitter 16 to illuminate a target 18 within the field of view of the binocular microscope 14. The position of the beamsplitter relative to its horizontal and vertical axes is determined by the micromanipulator apparatus according to this invention, designated generally by the reference numeral 17.

The apparatus 17 includes a control rod 20, shown in greater detail in FIG. 6, a control member 22, a ball joint 24, and a spring 26 connecting the control rod 20 to the control member 22 coupled to the spherical bearing assembly located to define a pivot point.

With the micromanipulator apparatus 17 according to the invention, the position of the beam splitter 16 relative to the beam from the slit lamp is determined by actuation of the control rod 20 by the control member 22 through the spherical bearing assembly and the coiled spring coupling. The control member 22 is coupled to a ball joint 24, best seen in FIG. 4, for freedom of movement in a plane having x and y components. Movement of the control member 22 is transmitted through the ball joint 24, the spring 26, and the control rod 20 to provide corresponding movements of the focused beam emanating from the beamsplitter 16 to the target 18. As mentioned, a feature of the invention is that the movement of the focused beam on the target corresponds directly to the direction of motion of the control member 22 when manipulated by the operator.

It is another feature of the invention to provide for automatic centering of the focused beam when manual control on the control member 22 has ceased. Such a feature is provided by the coiled spring 26 joining the control member 22 and the control rod 20. The spring characteristics of the spring 26 are such that the control member promptly and reliably returns to alignment with the outermost portion of the control rod 20 when the control member 22 is released.

Figure 2:
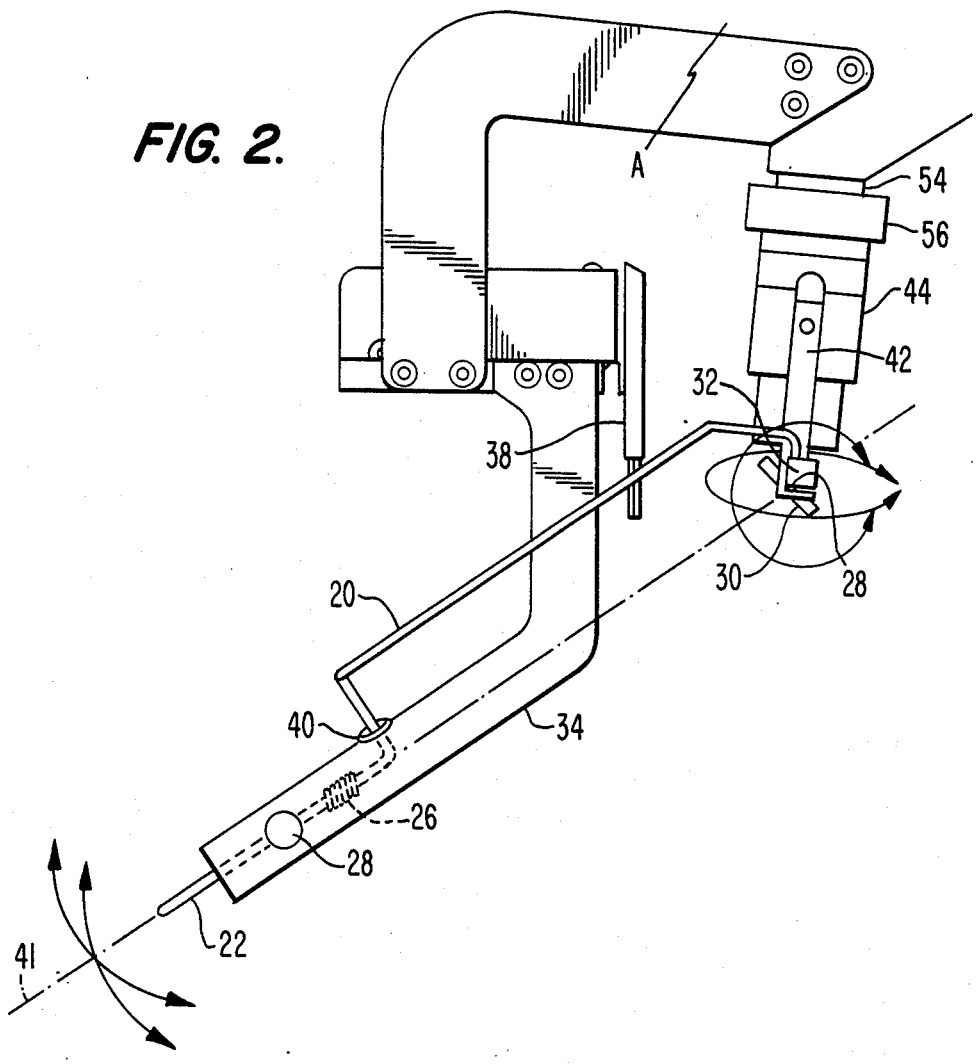
FIG. 2 is a detailed view of a portion of the apparatus shown in FIG. 1 which shows the beam control apparatus in greater detail.
Figure 3:
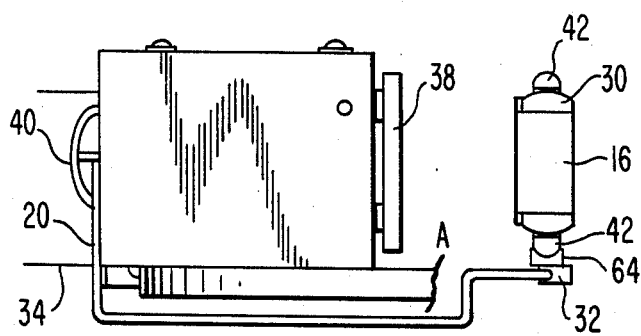
FIG. 3 is a pictorial view of the apparatus of FIG. 2 viewed from above with the turret section removed from line A—A to the beamsplitter hinge pins to illustrate a top view of portions of the micromanipulator or beam control apparatus according to the invention.
Figure 4:
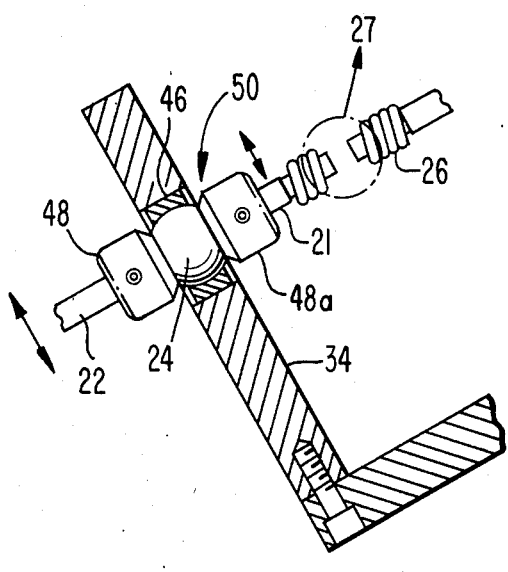
FIG. 4 is a detailed view of a portion of the apparatus of FIG. 1, partially in section, showing in detail the spherical ball joint and spring coupling between the control member and control rod of the apparatus.
Figure 5:
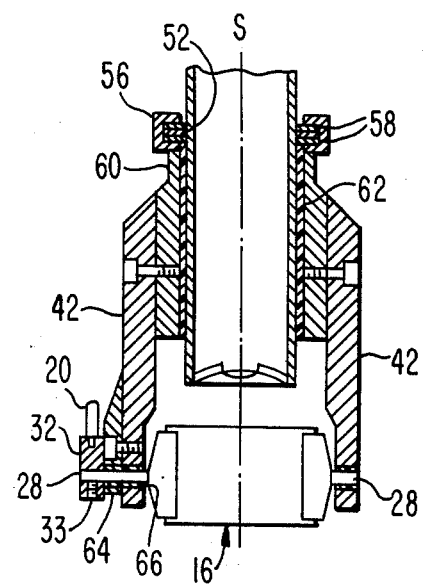
FIG. 5 is a sectional view of the gimbal assembly which supports the beam splitter taken along line B—B of FIG. 1.

As shown in FIGS. 2 and 5, the control rod 20 is secured by a clamp 32 to a hinge pin 28 on which the splitter support 30 is mounted and secured by a set screw 33. The ball joint 24, shown generally at numeral 29 in FIG. 2 and diagrammatically in FIG. 4 is supported by a control rod bracket 34 secured to the binocular microscope 14 immediately behind a shutter housing 36. The shutter housing 36 contains a shutter mechanism 38 which can be interposed between the beamsplitter 16 and the objective lens of the binocular microscope. As can be seen from FIG. 5, the control rod 20 is connected to the beamsplitter 16 at a point remote from its vertical axis of rotation to permit the rod to exert a torque about the vertical axis in order to deflect the beam in a horizontal direction. Similarly, the control rod 20 is attached to the clamp 32 at a point remote from the horizontal axis of rotation of the beamsplitter to provide an offset connection which permits it to exert a torque about the horizontal axis of the mirror of the beamsplitter and thus deflect the beam in a vertical direction.

Returning to FIG. 4, the ball joint 24 is secured by adhesive 46 to a control rod bracket 34 at a lower end of the micromanipulator according to the invention. An inset 50 between the surface of the control rod bracket 34 and the bearing 46 serves to prevent binding between the control rod bracket 34 and the adjacent collars 48, 48a secured to the control member 22 on each side of the ball joint 24. The collar 48 is secured by a set screw to the control member 22, the collar 48a is correspondingly secured to the control member 22. Movement of the control member extension 21 secured to the spring end in the upward direction denoted by the single-tipped arrow on the outboard side of the control rod bracket causes a corresponding downward movement on the inboard side of the control bracket, and vice versa, as denoted by the double-tipped arrow. Such upward movement of the outboard side of the control member 22 causes the inboard side of the control member 22 to deflect downwardly to cause a corresponding downward movement of the control rod 20 which causes the beamsplitter 16 to rotate counterclockwise about its horizontal axis to move the illumination on the target upwardly, i.e., in the same direction as the control member 22. Similarly, downward movement of the outboard side of the control member 22 causes an upward movement of the inboard side on the control member 22 and a corresponding upward movement of the control rod 20 causing a clockwise pivot of the beamsplitter 16 to drive the image on the target downwardly.

Rotational movement of the beamsplitter 16 about its vertical axis in accordance with leftward and rightward movement of the control member 22 can be understood with respect to FIGS. 2 and 5. A turret 44 is rotatably mounted on a flange 42 on a barrel 54 of the laser beam delivery assembly 12 by a retainer ring 56 which is offset from the flange 52 by a pair of thrust washers 58 which provide free rotation of the turret 44 about the barrel 54 and thus about the vertical axis s of the apparatus. A sleeve 60 extending downwardly from the retainer ring 56 is spaced from the barrel 54 by a low friction rotation bushing 62. A control rod support member 64 is interposed between the clamp 32 and the respective support arm 42 to insure clearance between the control rod 20 and the support arm 42. The hinge pin 28 is received in the control rod support and the support arm 42 in the low friction bearing 66. The low friction bearings 62 and 66 are made of a TEFLON brand material providing a wear and compression resistant bearing surface that insures smooth motion of the beamsplitter in response to movements of the control rod 20.

Thus, rightward movement of the control member 22, in a direction perpendicular to the plane of the drawings of FIGS. 2 and 4 causes a corresponding leftward movement of the control member on the inboard side of the control bracket which causes the rod 20 to rotate the beamsplitter rightwardly when viewed at the target 18, thus to cause a corresponding rightward movement of the focused beam on the target 18. Conversely, leftward movement of the inboard side of the control member causing the rod 20 to rotate the beamsplitter leftwardly, thus to cause a leftward movement of the focused beam on the target.

When used by a surgeon, the binocular microscope is first brought into rough alignment with target 18 using a positioning handle 68 and the slit lamp beam is then positioned within the target 18 using the control member 22. When the precise location on the target 18 for photocoagulation by the laser is illuminated by the beam from the laser beam delivery assembly 12, the surgeon operates the apparatus by actuating a trigger (not shown) to cause a beam from the laser 11 to pass through the laser beam delivery assembly 12 wherein it is made colinear with the binocular microscope in a manner well known to the art. The laser beam passes from the laser beam delivery assembly through the turret to the target 18. Simultaneously, before the laser beam from the argon laser 10 passes into the laser beam delivery assembly 12, the shutter 38 is actuated to prevent laser light reflected from the target 18 from passing back through the binocular microscope.

Figure 6B:
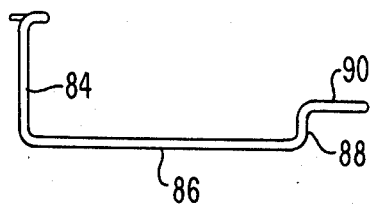
FIGS. 6a, 6b, and 6c respectively show side, top, and end views of the contour of the control rod used in the apparatus according to the invention.
Figure 6A:
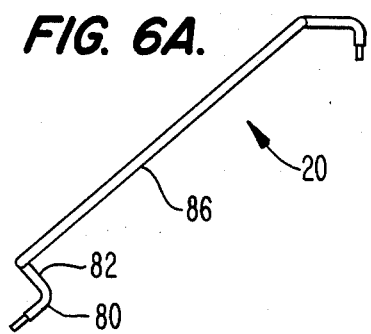
Figure 6C:
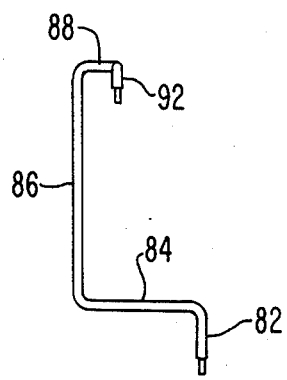

The contour of the control rod 20 is shown more specifically in FIGS. 6a–6c. Thus, the control rod 20 includes an outward end portion 80 to be secured to the coil spring 26 and which lies along an axis 41 coincident with the neutral position of the control member and the pivot axis of the apparatus. A first orthogonal portion 82 extends approximately orthogonally to the portion 80 to a distance sufficient to exit the control rod bracket 34 (as best seen in FIGS. 1 and 2) to a first offset portion 84 through an enlarged opening 41 to define a first torque arm relative to the beamsplitter 16. The portion 84 is secured to an extending portion 86 which, in FIGS. 1 and 2, lies approximately parallel to the axis 41 of the micromanipulator apparatus. A second portion 88 is secured to the extending portion 86 and to a portion 90, then downwardly through a portion 92 to be received in the bracket as described. The physical construction of the control rod 20, as described above and shown, permits connection through the coiled spring 26 to a pivot point defined at the spherical bearing 24 to the support structure of the gimballed beamsplitter 16 to permit sufficient rotational and pivoting torques to the beamsplitter to achieve the aims of the invention.

The invention may be embodied in other specific forms without departing from its spirit or essential characteristics. The present embodiments are, therefore, to be considered in all respects as illustrative and not restrictive, the scope of the invention being indicated by the claims rather than by the foregoing description, and all changes which come within the meaning and range of the equivalents of the claims are therefore intended to be embraced therein.

What is claimed is:

1. In an apparatus for micromanipulating a position of a light beam directed against a target of the type which includes a source of light and a beamsplitter for receiving light from said source and redirecting said light to said target, said beamsplitter being pivotable about an x-axis for vertically redirecting said light and rotatable about a y-axis for horizontally redirecting said light, means for manually micromanipulating said beamsplitter comprising;
    a control member capable of movement in a direction having an x-component and a y-component;
    a coiled spring coupled to said control member through a pivot location; and
    a control rod coupled to said spring and to said beamsplitter to exert a torque on said beamsplitter to redirect said light on said target in the same relative direction of movement as said control member, wherein the longitudinal axis of the control member, the longitudinal axis of said coiled spring, and the intersection of the pivotal and rotational axes of the beamsplitter lie on a straight line, when said control member is not manipulated.

2. The micromanipulating means as claimed in claim 1, further including a spherical bearing located at said pivot location intermediate said control member and said coiled spring.

3. The micromanipulating means of claim 1 wherein said coiled spring is respectively connected to said control member and to said control rod to cause said beamsplitter to return to a predetermined central location on its pivotal and rotational axes in the absence of manual force on said control member.

4. An apparatus for micromanipulating the position of a light beam directed toward a target, said apparatus comprising:
    a laser beam delivery assembly having an attenuated laser light source providing a first beam for illuminating an area on a target;
    a beamsplitter assembly having a beamsplitter for redirecting said first beam, said beamsplitter being rotatably and pivotably mounted on said beam delivery assembly;
    a control rod attached to said beamsplitter assembly in a predetermined neutral position for rotating and pivoting said beamsplitter so that the position of the beam on said target is shifted; and
    a coil spring coupling said control rod to a control member through a predetermined pivot position relative to said control member so that said control rod is deflected from said predetermined pivot position by said control member when said control member is moved and so that said control rod is returned to said predetermined position by said spring when said control member is released, and wherein the primary axis of said control member, said coil spring, and the intersection of a rotation axis of said beamsplitter are colinear.

5. The apparatus as claimed in claim 4, wherein said laser beam delivery assembly includes means for illuminating an area on said target located in an eye of a patient.

6. The apparatus as claimed in claim 4, wherein said laser beam delivery assembly comprises means for producing photocoagulation in an eye of a patient, said means producing a second beam, said second beam being redirected by said beamsplitter and aimed using said first beam.

7. The apparatus as claimed in claim 6, wherein said means for producing photocoagulation is a laser.

8. The apparatus as claimed in claim 6, wherein said means for producing photocoagulation is an arc lamp.

9. The apparatus as claimed in claim 4, further including a hinge pin for mounting said beamsplitter thereon, wherein said control rod is secured to said hinge pin on which said beamsplitter is mounted in a manner which permits torque to be exerted on said beamsplitter in response to movement of said control rod.

10. The apparatus as claimed in claim 4, further including a spherical bearing located intermediate said control member and said spring, wherein the primary axis of said control member, said coil spring, and the intersection of a rotation axis of said beamsplitter are colinear with said spherical bearing.

11. The apparatus as claimed in claim 10, wherein said control rod is structurally configured and defined to remain clear of the field of view of a microscope directed toward the reflection of said first beam from the eye of the patient and to exert a torque on said beamsplitter.

12. The apparatus as set forth in claim 4, further including a spherical bearing located intermediate said control member and said spring.

13. The apparatus as claimed in claim 12, wherein means including said control member, said spherical bearing, said rod, and said beamsplitter are structurally arranged for moving said light beam so that manipulative movement of said control member by an operator in any direction having respective leftward, rightward, upward, and downward components causes a corresponding relocation of said light beam on said target in a direction having corresponding leftward, rightward, upward, and downward components.

14. In an apparatus for micromanipulating a position of a light beam directed against a target, of the type which includes a source of light and a beamsplitter for receiving light from said source and redirecting said light to said target, said beamsplitter being pivotable about an x-axis for vertically redirecting said light and rotatable about a y-axis for horizontally redirecting said light, means for manually micromanipulating said beamsplitter comprising:
  a control member capable of movement in a direction having an x-component and a y-component;
  means, including a coiled spring coupled to said control member through a pivot location, for causing said beamsplitter to return to a predetermined control location on its pivotal and rotational axes in the absence of a force in said control member; and
  a control rod coupled to said spring and to said beamsplitter to exert a torque on said beamsplitter to redirect said light on said target in the same relative direction of movement as said control member, wherein the longitudinal axis of the control member, the longitudinal axis of the coiled spring, and the intersection of the pivotal and rotational axes of the beamsplitter lie on a straight line, when said control member is not manipulated.

15. The micromanipulating means as claimed in claim 14, further including a spherical bearing located at said pivot location intermediate said control member and said coiled spring.

* * * * *